(12) United States Patent
Pan

(10) Patent No.: US 10,857,270 B2
(45) Date of Patent: Dec. 8, 2020

(54) PUMP ARRANGEMENT FOR A DOUBLE BREAST PUMP, DOUBLE BREAST PUMP AND METHOD OF OPERATION

(71) Applicant: KONINKLIJKE PHILIPS N.V., Eindhoven (NL)

(72) Inventor: Yi Bing Pan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 296 days.

(21) Appl. No.: 15/769,088

(22) PCT Filed: Nov. 4, 2016

(86) PCT No.: PCT/EP2016/076659
§ 371 (c)(1),
(2) Date: Apr. 18, 2018

(87) PCT Pub. No.: WO2017/007029
PCT Pub. Date: May 11, 2017

(65) Prior Publication Data
US 2018/0303985 A1 Oct. 25, 2018

(30) Foreign Application Priority Data

Nov. 6, 2015 (WO) ................ PCT/CN2015/093990
Dec. 3, 2015 (EP) ..................................... 15197797

(51) Int. Cl.
*A61M 1/06* (2006.01)
*A61M 1/00* (2006.01)

(52) U.S. Cl.
CPC .......... *A61M 1/062* (2014.02); *A61M 1/0035* (2014.02); *A61M 1/06* (2013.01);
(Continued)

(58) Field of Classification Search
CPC ...... A61M 1/062; A61M 1/0035; A61M 1/06; A61M 1/066; A61M 2205/8206;
(Continued)

(56) References Cited

U.S. PATENT DOCUMENTS

| 5,810,772 A | 9/1998 | Niederberger |
| 6,355,012 B1 | 3/2002 | Nuesch |

(Continued)

FOREIGN PATENT DOCUMENTS

| CN | 202724325 U | 2/2013 |
| CN | 203736595 U | 7/2014 |

(Continued)

*Primary Examiner* — Bhisma Mehta
*Assistant Examiner* — Rachel T. Smith

(57) ABSTRACT

The present invention relates to a pump arrangement (1) for a double breast pump (2). The pump arrangement (1) comprises first and second terminals (23, 24) for connecting first and second expression kits (3, 4) having first and second breast shields (5, 6) and at least one container (7) for collecting breast milk (8) in fluidic connection with the expression kits (3, 4), a pump (9) for generating reduced pressure within said breast shields, a plurality of conduits (10, 11, 14, 15, 16), a suction valve (12) connected to the pump (9) by a connection conduit (14) and to the first and second terminals (23, 24) by respective air conduits (10, 11), and a venting valve (13) connected to the first and second terminals (23, 24) by venting conduits (15, 16), wherein the venting valve (13) comprises an opening (17) to the environment. The pump (9) is alternatingly connected to the first and second terminals (23, 24) by alternate opening and closing of the suction valve (12) and the venting valve (13).

21 Claims, 2 Drawing Sheets

(52) U.S. Cl.
CPC ..... *A61M 1/066* (2014.02); *A61M 2205/3337* (2013.01); *A61M 2205/50* (2013.01); *A61M 2205/502* (2013.01); *A61M 2205/8206* (2013.01)

(58) Field of Classification Search
CPC .... A61M 2205/3337; A61M 2205/502; A61M 2205/50
See application file for complete search history.

(56) References Cited

U.S. PATENT DOCUMENTS

| | | | |
|---|---|---|---|
| 6,383,163 | B1 | 5/2002 | Kelly |
| 6,997,897 | B1 | 2/2006 | Silver |
| 2003/0069536 | A1* | 4/2003 | Greter ............... A61M 1/06 604/74 |
| 2005/0283112 | A1* | 12/2005 | Britto ............... A61M 1/06 604/74 |
| 2008/0009815 | A1* | 1/2008 | Grabenkort ......... A61M 1/0068 604/346 |
| 2008/0177224 | A1* | 7/2008 | Kelly ............... A61M 1/06 604/74 |
| 2009/0099511 | A1* | 4/2009 | Sutrina ............... A61M 1/06 604/74 |
| 2010/0121266 | A1* | 5/2010 | Bryan ............... A61M 1/0072 604/74 |
| 2011/0270163 | A1* | 11/2011 | Britto ............... A61M 1/06 604/74 |

FOREIGN PATENT DOCUMENTS

| | | |
|---|---|---|
| EP | 0990445 A2 | 4/2000 |
| EP | 990445 A3 | 4/2014 |
| WO | 2014058430 A1 | 4/2014 |

\* cited by examiner

PUMP ARRANGEMENT FOR A DOUBLE BREAST PUMP, DOUBLE BREAST PUMP AND METHOD OF OPERATION

This application is the U.S. National Phase application under 35 U.S.C. § 371 of International Application No. PCT/EP2016/076659, filed on Nov. 4, 2016, which claims the benefit of International Application No. PCT/CN2015/093990 filed on Nov. 6, 2015 and International Application No. 15197797.2 filed on Dec. 3, 2015. These applications are hereby incorporated by reference herein.

FIELD OF THE INVENTION

The present invention relates to a pump arrangement for a double breast pump with alternating suction, to a double breast pump and to a method of operating such a pump arrangement.

BACKGROUND OF THE INVENTION

EP 0 990 445 A2 discloses a breast pump assembly for either single or double breast pumping which has first and second breast pump units. Each breast pump unit has a breast shield within which a breast is received, and at least one container for collecting breast milk expressed into a respective breast shield. A pumping mechanism, such as one having a battery power source, generates a periodic reduced pressure within the breast shields. The pumping unit is carried by the first breast pump unit. A mechanism is provided for alternating the periodic reduced pressure between the first and second breast pump units.

Known embodiments of breast pumps are often large and heavy due to the requirement of a high-performance pump to generate a suction which is sufficient to extract breast milk from both sides simultaneously. Besides that, simultaneous suction on both sides is often experienced as unnatural by lactating women.

SUMMARY OF THE INVENTION

It is an object of the present invention to provide a pump arrangement for a double breast pump with alternating suction, a double breast pump and a method of operating such a pump arrangement, which provide a more natural lactating experience for a lactating woman. Further, a light and compact size double breast pump shall be provided. FF In a first aspect of the present invention a pump arrangement for a double breast pump is presented, which comprises first and second terminals for connecting first and second expression kits having first and second breast shields and at least one container for collecting breast milk in fluidic connection with the expression kits, a pump for generating reduced pressure within said breast shields, a plurality of conduits, a control unit for controlling operating parameters of the breast pump, a suction valve connected to the pump by a connection conduit and to the first and second terminals by respective air conduits, and a venting valve connected to the first and second terminals by venting conduits, wherein the venting valve comprises an opening to the environment, wherein the suction valve and the venting valve are 3-way-valves each having three inlets and/or outlets, and wherein the pump is alternatingly connected to the first and second terminals by alternate opening and closing the suction valve and the venting valve.

The pump assembly according to the EP 0 990 445 A2 is based on a rotating disc opening and closing air conduits. Mechanical pumps generally are prone to vibrations, noise development and mechanical faults like jamming. The higher the suction strength, the larger and heavier the pump assembly has to be. Besides that, pumps of this size normally cannot be operated by batteries and need a connection to the electric supply network. This restricts flexibility of use. Thus, mechanical pumps are uncomfortable to use in many respects.

The present invention is based on the idea to replace the mechanism of the known breast pump by an arrangement of two valves and a plurality of conduits. This enables a flexible control of the operational parameters of the pump, for example the duration of the suction cycle, the frequency of suction, the strength of suction, etc., thus giving a more natural lactating experience to the lactating woman. Besides, an easy setup for the pump arrangement with a small number of components and little disposition to faults can be achieved. The control unit allows easy adaption of the operational parameters to match the need with respect to health and well-being of the user since the needs of the user can differ considerably.

The pump arrangement according to the invention thus represents a simple solution to provide alternate suction exerted to the expression kits of a double breast pump. The pump itself can be small and thus light and has less power consumption due to the fact that at a time only one of the connections to the two expression kits is under suction. A smaller pump is less expensive and can be operated at a lower noise and vibration level. Small valves help to keep the system flexible and lightweight by reduction of pump size, power consumption and total weight of the breast pump due to fewer and lighter components.

In another aspect of the present invention, a double breast pump is presented which comprises first and second expression kits having first and second breast shields, at least one container for collecting breast milk in fluidic connection with the expression kits, and a pump arrangement connected to the first and second expression kits.

The proposed breast pump comprising detachable expression kits is easy to handle and clean, and can be equipped with different expression kits depending on the needs of the user. Faulty, old, or unsuitable expression kits can be discarded and replaced at low cost. The expensive pump arrangement can be maintained.

In a further aspect of the present invention a method for operation of a pump arrangement for a double breast pump is presented, in which in a first operational state the first terminal is connected with the pump via the suction valve and performing suction, and simultaneously the second terminal is connected with the venting valve, in a second operational state the second terminal is connected with the pump via the suction valve and performing suction, and simultaneously the first terminal is connected with the venting valve, and the first and second operational state are alternatingly changed.

The alternating actuation of the terminals and thus of the connected expression kits gives a natural impression to the user of the double breast pump which is similar to normal breast-feeding. The arrangement of two valves and a plurality of conduits and the alternating suction and venting allows flexible control of the operational parameters of the pump, for example duration of suction cycle, frequency of suction, suction strength etc., thus giving a more natural experience to the lactating woman.

In yet further aspects of the present invention, there is provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, breast pump, computer program and medium have similar and/or identical preferred embodiments as the claimed pump arrangement, in particular as defined in the dependent claims and as disclosed herein.

According to another embodiment of the invention, the venting conduits are connected to the air conduits by first and second intersections which are connected to the first and second terminals. The intersections allow easy assembly and disassembly in case of damage or for cleaning or replacement of the expression kits.

In a first operational state the first terminal is in air-ducting connection with the pump via the suction valve and performing suction, and the second terminal is simultaneously in air-ducting connection with the venting valve.

In a second operational state the second terminal is in air-ducting connection with the pump via the suction valve and performing suction, and the first terminal is simultaneously in air-ducting connection with the venting valve.

Advantageously, the pump is an electrically driven pump and the suction and venting valves are solenoid valves. These known components are reasonably priced, easily available and reliable in operation.

Preferably, the operating parameters comprise one or more of the strength of suction, the pumping frequency, the duration of the pumping cycle, and the differential quotient of the suction pressure over time. The strength of the suction is especially important to control since the breasts of feeding mothers often are algesic or sore. High suction can lead to pain and indisposition. Pumping cycles which are too long or frequencies which are too high can also lead to pain which can be avoided by the control of said parameters. A variation of the differential quotient dp/dt (resulting in a kind of speed ramping) of the pressure p(t) over time t can further improve a natural feeling for users of the breast pump by varying the curve profile of the suction.

According to an advantageous embodiment, the control unit further comprises one or more of a clock, a timer, and an alarm clock. These functions can help to support the user in using the double breast pump effectively, e.g. by reminding to use the breast pump regularly at specific times etc.

Preferably the control unit comprises a user interface. This allows the user of the arrangement to control operational parameters of the arrangement or to derive useful information about the device or the operational parameters.

Advantageously, the user interface comprises a display for displaying information to a user of the assembly and actuating elements to adjust the operating parameters of the assembly. The user is guided and supported by information given on the display and by the easy possibility to choose operation values and other parameters to the person's liking.

According to yet another embodiment of the invention, the change between the first and second operational state takes place at a fixed frequency or at variable frequency. In a simple and cost-effective embodiment of the pump arrangement according to the present invention, the change between the operational states of suction and venting can be fixed to a specific value or controlled and varied by an integrated circuit which is housed in the assembly without user control.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE EMBODIMENTS

Figure 1:
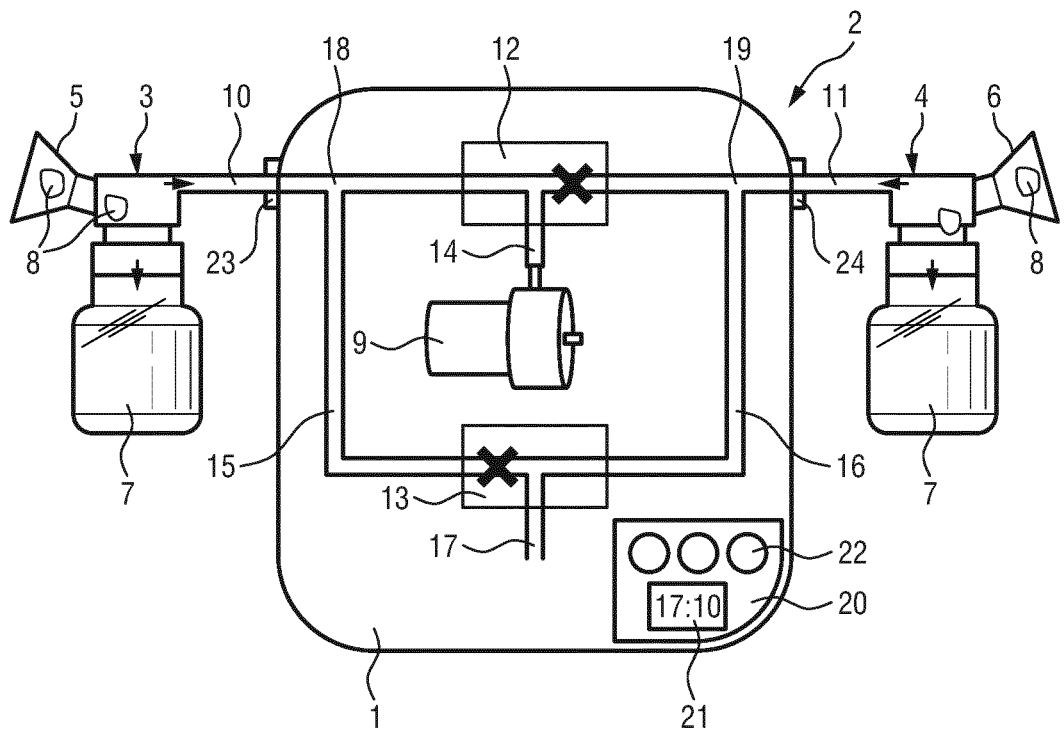
FIG. 1 shows a schematic view of a preferred embodiment of the double breast pump including a pump arrangement according to the present invention.

FIG. 1 shows a preferred embodiment of a pump arrangement 1 for a double breast pump 2 according to the invention. The double breast pump 2 comprises first and second expression kits 3, 4, wherein each of the expression kits 3, 4 comprises a breast shield 5, 6. The breast shields 5, 6 are formed to receive a lactating woman's breast and to collect breast milk 8 extracted from the breast by the double breast pump 2.

In the embodiment shown in FIG. 1, each of the expression kits 3, 4 comprises its own container 7 to collect the breast milk 8. Alternatively, it is possible to connect the first and second expression kits 3, 4 and to collect the milk 8 in one single container 7. The container/containers 7 can be arranged in any suitable position.

The expression kits 3, 4 can especially be designed like expression kits known from the state of the art.

The assembly 1 further comprises a pump 9 which for example can be an electrically driven pump 9. The pump can be connected to an external power source or contain a battery or the like. Especially the equipment with a battery allows a slim, compact and lightweight design of the double breast pump 2. The pump 9 can also be designed similar to known pump devices, which are generating a negative pressure (suction). A detailed description of the pump 9 therefore is deemed obsolete here.

Normally, the first and second expression kits 3, 4 are connected to the pump 9 by way of air conduits 10, 11. These air conduits 10, 11 are connected to an outlet of the pump 9 by way of a connection conduit 14.

In the preferred embodiment of the invention, the expression kits 3, 4 are connected to the pump arrangement 1 by way of first and second terminals 23, 24. The terminals 23, 24 can e.g. be arranged directly on the pump arrangement 1, as shown in FIG. 1, but they can also be designed as additional intersections in the air conduits 10, 11, e.g. within or outside of a housing of the pump arrangement. For instance, a coupling (e.g. like a socket) may be provided at the end of the air conduits 10, 11, to which a corresponding coupling (e.g. like a plug) of the expression kits 3, 4 can be coupled. Further, the terminals 23, 24 can be part of the expression kits 3, 4, for example for connecting the air conduits 10, 11 to the upper part of the expression kits 3, 4. The terminals 23, 24 are advantageous with regard to handling, cleaning and storing the double breast pump 2. Besides that, the expression kits 3, 4 can be replaced when they are for example faulty, not suitable for the respective breast size or not hygienic any more. By way of the terminals 23, 24 the expensive pump arrangement 1 can generally be used with any expression kit which is available as cheap spare part.

The pump arrangement 1 according to the invention further comprises a suction valve 12 and a venting valve 13. The suction valve 12 is on the one hand connected to the pump 9 by way of the connection conduit 14 and to the expression kits 3, 4 by way of the air conduits 10, 11. The venting valve 13 is connected to the expression kits 3, 4 by way of venting conduits 15, 16. The venting conduits 15, 16 are connected to the air conduits 10, 11 by intersections 18, 19.

Each expression kit 3, 4 preferably comprises a single way valve, whose function is to seal the breast shield 5, 6 at its bottom when the respective breast shield 5, 6 is connected with the suction valve 12, and to let breast milk 8 go through to the at least one container 7 when the respective breast shield 5, 6 is connected with the venting valve 13. The single way valves can for example be known flap valves.

The suction valve 12 and the venting valve 13 are both designed as three-way-valves. The valves accordingly comprise three inlets/outlets respectively each of which allows, when interconnected, air to flow along different pathways in the pump arrangement 1 by opening and closing the respective inlets and outlets of the valves.

Suction valve 12 is connected, on the one hand to the connection conduit 14 which connects to the pump 9, and on the other hand suction valve 12 connects to the expression kits 3, 4 by way of the air conduits 10, 11.

Venting valve 13 comprises three outlets and includes connections only to the venting conduits 15, 16 which eventually connect with the expression kits 3, 4. A third outlet is without a connection and opens via an opening 17 to the environment of the breast pump 2. The opening 17 is the venting opening used for venting the respective part of the pump arrangement 1 which is in venting status.

The pump arrangement 1 can further comprise a control unit 20, which for example might be arranged in the pump arrangement 1 itself in a respective housing or alternatively separated from the pump arrangement 1 as a separate device.

The control unit may comprise a display 21 and one or more actuating elements 22. The control unit 20 allows the user of the double breast pump 2 to control several operating parameters of the pump arrangement 1. Operating parameters which are useful to control are for example the strength of the suction, the pumping frequency and the length of a pumping cycle. Lactating women often suffer from painful breasts or nipples during breast feeding. Thus it is useful to allow the user to adjust, especially to reduce the suction force to remain pain free. Likewise, the length of the pumping cycle and the pumping frequency could be adapted to the user's needs. Adaptable longer or shorter pumping cycles and pumping frequencies can offer more comfort for different users and their needs.

Another useful parameter to control and to modify if applicable is the differential quotient dp/dt of the suction pressure p(t), that is, the variation of the suction pressure p, over time t. Hence, the pump might reach its maximum suction in a linear way over time. Alternatively, the pump might increase its capacity in the beginning and reduce the capacity in the end of the cycle. Likewise, it is possible to modify the differential quotient the other way around. Variation of the differential quotient results in a more curved suction profile over time, again creating a more natural feeling whilst using the breast pump 2.

To allow further control to the pumping of breast milk 8 by the double breast pump 2, the control unit 20 can comprise for example a clock, a timer and/or an alarm clock which can be adjusted to the users' needs.

On the display 21, relevant information can be conveyed to the user. There can for example be a sensor for the amount of milk 8 which has been expressed, and on the display 21 the amount of milk in the one or more container 7 can be displayed. It is also possible to display information about previous use, operational parameters, time of use etc. depending on the equipment incorporated in the control unit 20.

Alternatively, the double breast pump 2 can be realized without control unit 20 to provide a cheap and rugged version e.g. for traveling. In this case, the operational parameters like suction force, cycle length and frequency can be set to typical values which can be derived from studies and data collections. They cannot be adapted by the user. The opening and closing of the valves 12, 13 is then controlled by an integrated circuit which is arranged somewhere suitable in the pump arrangement 1.

The combination of the suction valve 12 and the venting valve 13 allows alternating operation of the double breast pump 2, as is described in more detail in the following FIGS. 2 and 3A to 3B.

Figure 2:
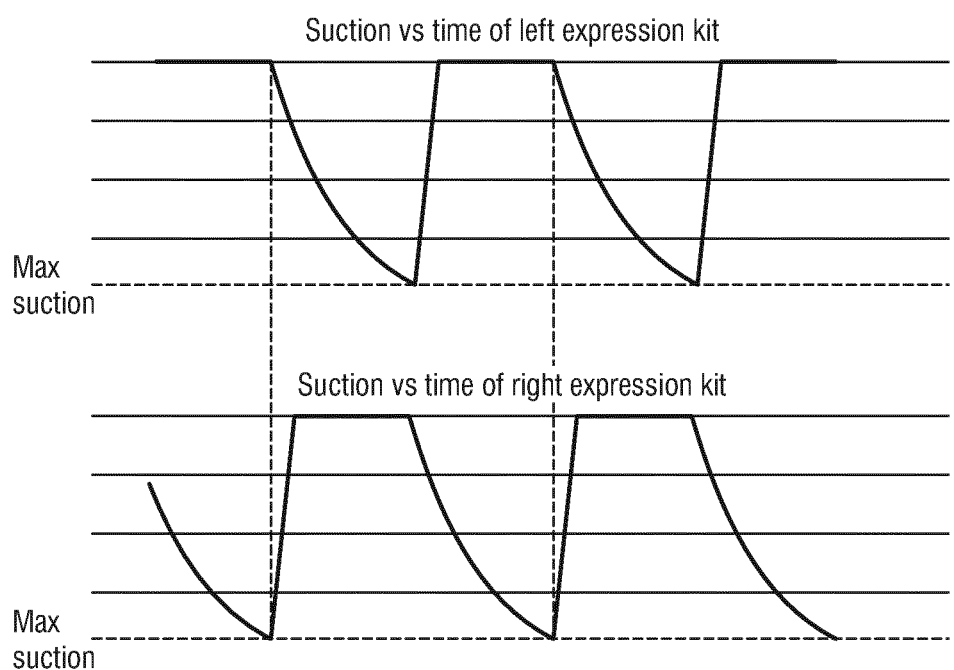
FIG. 2 shows a chart of the suction versus time of the breast pump assembly according to the invention.

Referring now to FIG. 2, it is apparent that each of the expression kits 3, 4 can be alternatingly pressurized and vented by way of opening and closing the air conduits 10, 11 and the venting conduits 15, 16 by opening and closing the respective outlets or inlets of the suction valve 12 and the venting valve 13. As can be seen from FIG. 2, the maximum suction in the first expression kit 3 reaches its maximum when the second expression kit 4 is vented. Accordingly, when the second expression kit 4 is on maximum suction, the first expression kit 3 is vented. This allows a very comfortable and especially a natural feeling for the lactating woman. Additionally, the suction and venting valves 12, 13 are small, lightweight and cheap and thus allowing for a very small double breast pump 2 with the possibility of comfortable handling.

The function of the double breast pump 2 will now be described in more detail with reference to FIGS. 3A and 3B.

The pump 9 continuously generates negative pressure. The function of the suction valve 12 is to guide the airstream to the first or the second expression kit 3, 4 and simultaneously to close the side of the respective expression kit 3, 4 which is not under suction. The function of the venting valve 13 is to vent the first or the second expression kit 3, 4 which is currently not under suction and to close the side which is under suction to venting.

Figure 3A:
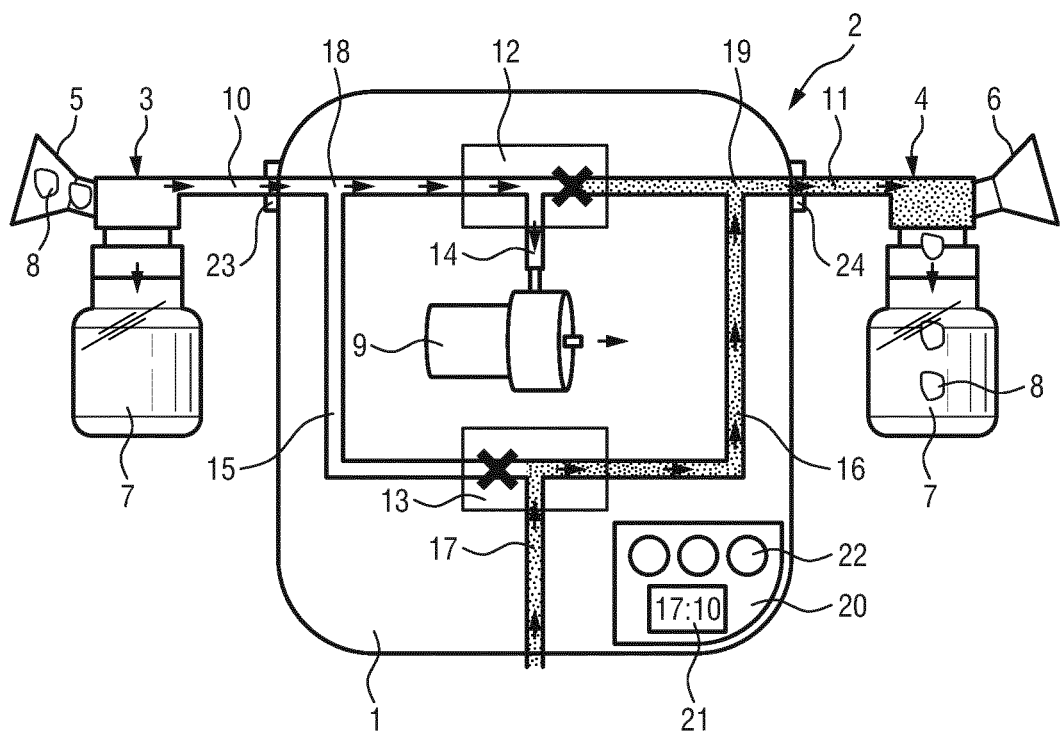
FIGS. 3A and 3B shows the double breast pump depicted in FIG. 1 in first and second operational states.

In FIG. 3A the air conduit 11 from the suction valve 12 to the second expression kit 4 is closed. Likewise, the venting conduit 15 from the venting valve 13 to the first expression kit 3 is also closed. The negative pressure or suction generated by the pump 9 activates the first expression kit 3, thus by way of the breast shield 5 sucking milk 8 from the lactating woman's breast. At the same time, the second expression kit 4 is vented, thus allowing the collected milk 8 to flow into the container 7.

Figure 3B:
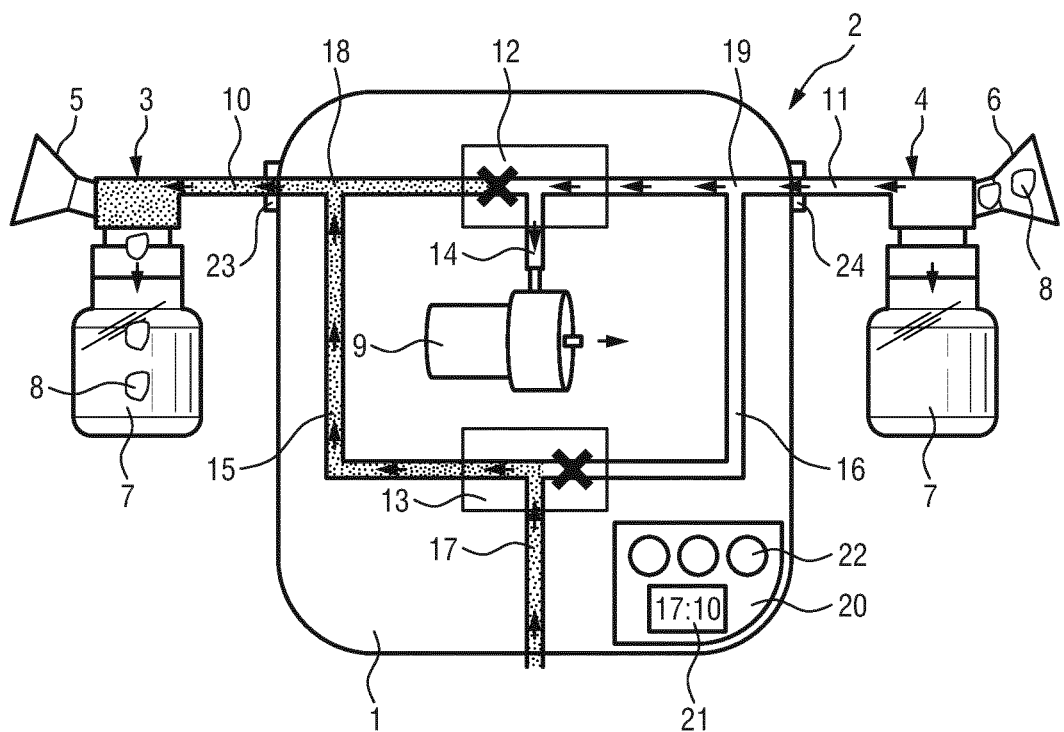

In FIG. 3B, the second operational state is shown. Here, the air conduit between the first expression kit 3 and the suction valve 12 is closed and the air conduit 11 between the suction valve and the second expression kit 4 is open.

Likewise, the venting conduit 16 between the venting valve 13 and the second expression kit 4 is closed and the venting conduit 15 between the venting valve 13 and the first expression kit 3 is open. The negative pressure exerted by the pump 9 is directed to the second expression kit 4, and milk 8 can be extracted from the other breast of the lactating woman. Simultaneously, the first expression kit 3 is vented.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A pump arrangement for a double breast pump, said pump arrangement comprising:
    first and second terminals for connecting first and second expression kits having first and second breast shields and at least one container for collecting breast milk in fluidic connection with the expression kits, wherein the first and second terminals are arranged directly on the pump arrangement;
    a pump for generating a continuous negative pressure within said breast shields;
    a control unit for controlling operating parameters of the double breast pump;
    a suction valve connected to the pump by a connection conduit and to the first and second terminals by a respective one of a first air conduit or a second air conduit, and configured to guide an airstream to one of the first and second expression kits under suction whilst simultaneously closing a side of one of the first and second expression kits which is not under suction; and
    a venting valve connected to the first and second terminals by one of a first venting conduit or a second venting conduit, and configured to vent one of the first and second expression kits which is not currently under suction and simultaneously close a side of one of the first and second expression kits which is under suction to venting,
    wherein the venting valve further comprises an opening to an environment;
    wherein the suction valve and the venting valve are each 3-way-valves each having three inlets and/or outlets;
    a first intersection coupling the first air conduit with the first venting conduit;
    a second intersection coupling the second air conduit with the second venting conduit,
    wherein the pump is configured to being alternatingly connected to the first and second terminals by alternate opening and closing of the suction valve and the venting valve;
    wherein in a first operational state, the first terminal is in air-ducting connection with the pump via the suction valve and performing suction and the second terminal is simultaneously in air-ducting connection with the venting valve via the second venting conduit and the second air conduit;
    wherein in a second operational state, the second terminal is in air-ducting connection with the pump via the suction valve and performing suction and the first terminal is simultaneously in air-ducting connection with the venting valve via the first venting conduit and the first air conduit;
    wherein the first and second operational states are alternatingly changed;
    wherein the first expression kit is on maximum suction when the second expression kit is vented; and
    wherein the second expression kit is on maximum suction when the first expression kit is vented.

2. The pump arrangement according to claim 1, wherein the first and second intersections are connected to the first and second terminals.

3. The pump arrangement according to claim 1, wherein the pump is an electrically driven pump and the suction and venting valves are solenoid valves.

4. The pump arrangement according to claim 1, wherein the operating parameters comprise one or more of a strength of a vacuum and a pumping frequency.

5. The pump arrangement according to claim 1, wherein the control unit comprises one or more of a clock, a timer, and an alarm clock.

6. The pump arrangement according to claim 1, wherein the control unit comprises a user interface.

7. The pump arrangement according to claim 6, wherein the user interface comprises a display for displaying information to a user of the double breast pump and actuating elements to adjust the operating parameters of the double breast pump.

8. The pump arrangement according to claim 1, wherein the change between the first and second operational states takes place at a fixed frequency or at a variable frequency.

9. The pump arrangement according to claim 1, wherein the operating parameters comprise one or more of a duration of a pumping cycle and a differential quotient of a suction pressure over time.

10. The pump arrangement according to claim 9, wherein the differential quotient of the suction pressure is varied linearly over time.

11. The pump arrangement according to claim 9, wherein the differential quotient of the suction pressure is varied over time by increasing a pump capacity in a beginning stage of the pumping cycle and reducing said pump capacity at an end stage of the pumping cycle.

12. The pump arrangement according to claim 9, wherein the differential quotient of the suction pressure over time is varied by reducing a pump capacity in a beginning stage of the pumping cycle and increasing said pump capacity at an end stage of the pumping cycle.

13. A double breast pump comprising:
    first and second expression kits having first and second breast shields,
    at least one container for collecting breast milk in fluidic connection with the first and second expression kits, and
    a pump arrangement connected to the first and second expression kits, comprising:
    first and second terminals for connecting to said first and second expression kits having said first and second breast shields and at least said one container for collecting breast milk in fluidic connection with the expression kits, wherein the first and second terminals are arranged directly on the pump arrangement;

a pump for generating a continuous negative pressure within said breast shields;

a control unit for controlling operating parameters of the double breast pump;

a suction valve connected to the pump by a connection conduit and to the first and second terminals by a respective one of a first air conduit or a second air conduit, and configured to guide an airstream to one of the first and second expression kits under suction whilst simultaneously closing a side of one of the first and second expression kits which is not under suction; and a venting valve connected to the first and second terminals by one of a first venting conduit or a second venting conduit, and configured to vent one of the first and second expression kits which is not currently under suction and simultaneously close a side of one of the first and second expression kits which is under suction to venting, a first intersection coupling the first air conduit with the first venting conduit;

a second intersection coupling the second air conduit with the second venting conduit, wherein the venting valve further comprises an opening to an environment;

wherein the suction valve and the venting valve are each 3-way-valves each having three inlets and/or outlets;

wherein the pump is configured to being alternatingly connected to the first and second terminals by alternate opening and closing of the suction valve and the venting valve;

wherein in a first operational state, the first terminal is in air-ducting connection with the pump via the suction valve and performing suction and the second terminal is simultaneously in air-ducting connection with the venting valve via the second venting conduit and the second air conduit;

wherein in a second operational state, the second terminal is in air-ducting connection with the pump via the suction valve and performing suction and the first terminal is simultaneously in air-ducting connection with the venting valve via the first venting conduit and the first air conduit;

wherein the first and second states are alternatingly changed;

wherein the first expression kit is on maximum suction when the second expression kit is vented; and wherein the second expression kit is on maximum suction when the first expression kit is vented.

14. The double breast pump according to claim 13, wherein the change between the first and second operational states takes place at a fixed frequency or at a variable frequency.

15. The double breast pump according to claim 13, wherein the operating parameters comprise one or more of a duration of a pumping cycle and a differential quotient of a suction pressure over time.

16. The pump arrangement according to claim 15, wherein the differential quotient of the suction pressure is varied linearly over time.

17. The pump arrangement according to claim 15, wherein the differential quotient of the suction pressure is varied by increasing a pump capacity in a beginning stage of the pumping cycle and reducing said pump capacity at an end stage of the pumping cycle.

18. The pump arrangement according to claim 15, wherein the differential quotient of the suction pressure is varied by reducing a pump capacity in a beginning stage of the pumping cycle and increasing said pump capacity at an end stage of the pumping cycle.

19. A method for operating a pump arrangement for a double breast pump, said method comprising:

in a first operational state, connecting a first terminal of the pumping arrangement with a pump via a suction valve and performing suction whilst closing an air conduit of the pumping arrangement from the suction valve to a second expression kit and simultaneously connecting a second terminal of the pumping arrangement with a venting valve via a second venting conduit;

in a second operational state, connecting the second terminal of the pumping arrangement with the pump via the suction valve and performing suction whilst closing the air conduit from the suction valve to a first expression kit and simultaneously connecting the first terminal with the venting valve via a first venting conduit;

wherein the pump applies a continuous negative pressure in the first operational state and in the second operational state;

wherein the first and second operational states are alternatingly changed;

wherein the first expression kit is on maximum suction when the second expression kit is vented; and wherein the second expression kit is on maximum suction when the first expression kit is vented.

20. The method according to claim 19, wherein the change between the first and second operational state takes place at a fixed frequency or at variable frequency.

21. A computer-readable storage medium that is not a transitory propagating signal or wave, the medium containing control information for controlling the method for operating the pump arrangement for the double breast pump as claimed in claim 19 where said control information is carried out on a computer.

* * * * *